US00PP21794P3

(12) United States Plant Patent
Bruinen

(10) Patent No.: US PP21,794 P3
(45) Date of Patent: Mar. 22, 2011

(54) ***CLUSIA* PLANT NAMED 'WHISTAR'**

(50) Latin Name: *Clusia rosea*
Varietal Denomination: Whistar

(76) Inventor: Edward Bruinen, Maasdijk (NL)

( * ) Notice: Subject to any disclaimer, the term of this patent is extended or adjusted under 35 U.S.C. 154(b) by 0 days.

(21) Appl. No.: 12/459,816

(22) Filed: Jul. 7, 2009

(65) Prior Publication Data

US 2011/0010811 P1 Jan. 13, 2011

(51) Int. Cl.
*A01H 5/00* (2006.01)

(52) U.S. Cl. ..... Plt./226; Plt./373

(58) Field of Classification Search ..... Plt./226, Plt./373, 216
See application file for complete search history.

(56) References Cited

PUBLICATIONS

Upov-rom GTITM Plant Variety Database 2010/02, GTI Jouve Retrieval Software, Citation for *Clusia* 'White Star' one page.*

* cited by examiner

*Primary Examiner*—June Hwu

(57) ABSTRACT

A new and distinct *Clusia rosea* cultivar named 'WHISTAR' is disclosed, characterized by unique variegated leaves, strong branching and an upright, pyramidal plant habit. The new variety is a *Clusia rosea,* suitable for indoor potted plant production.

1 Drawing Sheet

Figure 1:
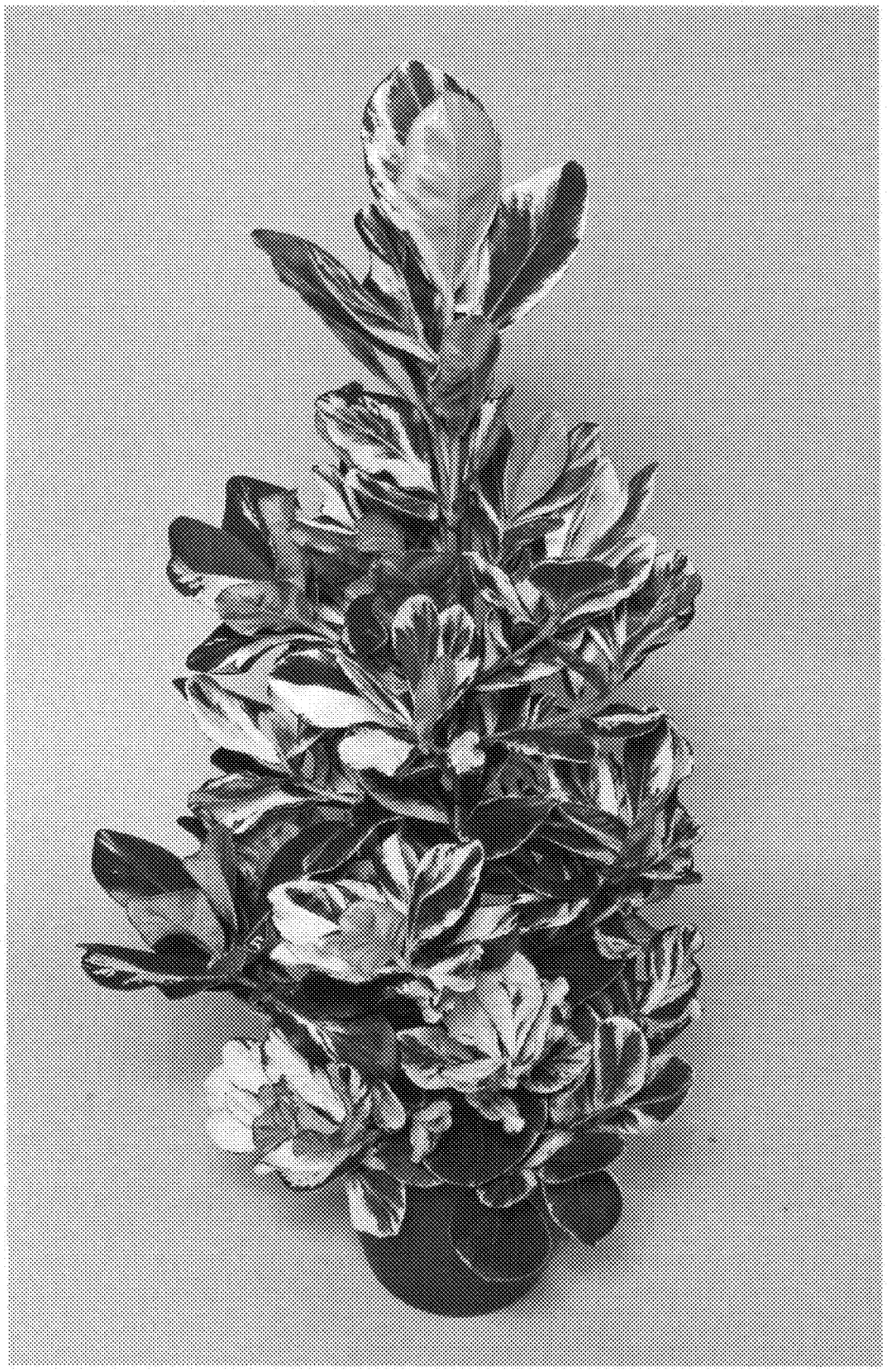

Latin name of the genus and species: *Clusia rosea.*
Variety denomination: 'WHISTAR'.

BACKGROUND OF THE INVENTION

The new cultivar was discovered as a chance, naturally occurring whole plant mutation of the parent variety, an unnamed, unpatented selection of *Clusia rosea.* 'Whistar' was discovered by Edward Bruinen, a citizen of the Netherlands in a commercial planting of *Clusia rosea* in February of 2003, at a commercial greenhouse in Maasdijk, The Netherlands.

Asexual reproduction of the new cultivar 'WHISTAR' by vegetative cuttings was first performed in Maasdijk, the Netherlands at a commercial greenhouse in June 2003 and has shown that the unique features of this cultivar are stable and reproduced true to type through successive generations.

SUMMARY OF THE INVENTION

The cultivar 'WHISTAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WHISTAR' These characteristics in combination distinguish 'WHISTAR' as a new and distinct *Clusia rosea* cultivar:

1. Unique variegated leaves.
2. Strong branching.
3. Upright pyramidal plant habit.

PARENT COMPARISON

Plants of the new cultivar 'WHISTAR' are similar to plants of the parent variety *Clusia roseas* in most horticultural characteristics. However, plants of the new cultivar 'WHISTAR' produce variegated foliage and stems whereas the parent variety has entirely green leaves and stems. Additionally, the new variety has a slightly slower growth rate than the parent variety.

COMMERCIAL COMPARISON

*Clusia rosea* 'Whistar' can be compared to the commercial variety *Clusia rosea* 'Variegata.' The two varieties are similar in most horticultural characteristics, however, *Clusia* 'Whistar' varies in having a different leaf color. *Clusia* 'Whistar' foliage color is Yellow-Green and Green, whereas the leaf color of 'Variegata' is Yellow and Green. Additionally, the variegation pattern is different, and the petiole attachment is different. Leaves of 'Whistar' are stronger, and more resistant to breakage than 'Variegata' and the leaves of 'Variegata' drop easily under stress conditions, compared to 'Whistar.'

BRIEF DESCRIPTION OF THE PHOTOGRAPH

The accompanying photograph in FIG. 1 illustrates in full color a typical plant of 'WHISTAR' grown in a greenhouse. The pot size is a commercial 15 cm container. The plant shown is approximately 8 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'WHISTAR' plants grown in a commercial greenhouse in Maasdijk, The Netherlands from Fall to Spring. The growing temperature ranged from approximately 17 to 18° C. at night and 20 to 22° C. during the day. Measurements and numerical values represent averages of typical flowering types. No chemical or photoperiodic treatments were given.
Botanical classification: *Clusia rosea* 'WHISTAR'.

PROPAGATION

Time to rooting: About 20 days at approximately 22° C.
Root description: Small, fleshy, free-branching roots.

PLANT

Growth habit: Upright, pyramidal.
Height: Approximately 105 cm.
Plant spread: Approximately 65 cm.
Growth rate: Rapid. Approximately 10 cm per month while actively growing.
Branching characteristics: Moderately branching, lateral branches grow from a single main stem.
Length of lateral stems: Average 16.8 cm.
Diameter of stems: Approximately 0.7 cm.
Quantity of lateral stems: Average 16.
Internode length: Average 4.2 cm.
Texture of stems: Rounded, smooth, moderately glossy.
Stem pubescence: None.
Color of stems: Near RHS Yellow-Green 143A, with stripes of both Yellow-Green 145A and Yellow-Green 150C.
Aspect: Straight.
Stem strength: Very strong.
Number of leaves per lateral branch: Average 10.
Other stem characteristics: None.
Age of plant described: Approximately 8 months old.
Pot size of plant described: Approximately 15 cm.

FOLIAGE

Leaf:
- *Arrangement.*—Opposite, simple.
- *Average length.*—Approximately 15.4 cm.
- *Average width.*—Approximately 8.7 cm.
- *Shape of blade.*—Obovate.
- *Aspect.*—Mainly flat and rigid, slight undulation near margins.
- *Apex.*—Obtuse.
- *Base.*—Shortened attenuate.
- *Attachment.*—Stalked.
- *Margin.*—Entire.
- *Texture of top surface.*—Smooth, glossy, leathery.
- *Texture of bottom surface.*—Smooth, glossy, leathery.
- *Color.*—Young foliage upper side: Irregularly marbled with background color near RHS Green 143A and 143B and also Green 144A. Blotches colored Yellow-Green 144A, 144C and 145D. Young foliage under side: Irregularly marbled with background color near RHS Green 143A and 143B. Blotches colored Yellow-Green 150B and 150C. Mature foliage upper side: Irregularly marbled with background color near RHS Green 137A. Blotches colored Yellow-Green 146A, 145D and 150D. Mature foliage under side: Irregularly marbled with background color near both RHS Yellow-Green 144A and 144B. Blotches colored Yellow-Green 150B.
- *Venation.*—Type: Pinnate. Color upperside: Near RHS Yellow-Green 144C. Color underside: Near RHS Yellow-Green 145D.

Petiole:
- *Length.*—Average 0.5 cm.
- *Width.*—Average 0.6 cm.
- *Coloration.*—Near RHS Yellow-Green 144C.
- *Petiole surface texture.*—Upper: Smooth. Lower: Smooth.

Other Characteristics: Foliage highly resistant to tearing or breaking due to mechanical stress. No stipules, tendrils, thorns, or spines present.

FLOWER

Bud production and flower production has not been observed to date.

REPRODUCTIVE ORGANS

Not observed due to lack of flower production.

OTHER CHARACTERISTICS

Disease resistance: Neither resistance nor susceptibility to diseases or pests has been observed in this variety.
Drought tolerance and temperature tolerance: Tender perennial, low temperature tolerance is unknown. Tolerates high temperature to at least 40° C. No drought tolerance has been observed.
Fruit/seed production: Fruits and seeds have not been observed.

What is claimed is:

1. A new and distinct cultivar of *Clusia* plant named 'WHISTAR' as herein illustrated and described.

* * * * *